United States Patent
Mathiowetz et al.

(10) Patent No.: US 9,864,357 B2
(45) Date of Patent: Jan. 9, 2018

(54) HANDHELD FIELD MAINTENANCE TOOL WITH INTEGRATION TO EXTERNAL SOFTWARE APPLICATION

(75) Inventors: Brad N. Mathiowetz, Lakeville, MN (US); Christopher P. Kantzes, Minneapolis, MN (US); Todd M. Toepke, Eden Praire, MN (US); Kun Yang, Eden Prairie, MN (US); Adam E. Lund, St. Louis Park, MN (US)

(73) Assignee: Fisher-Rosemount Systems, Inc., Austin, TX (US)

( * ) Notice: Subject to any disclaimer, the term of this patent is extended or adjusted under 35 U.S.C. 154(b) by 731 days.

(21) Appl. No.: 13/191,630

(22) Filed: Jul. 27, 2011

(65) Prior Publication Data
US 2012/0046911 A1    Feb. 23, 2012

Related U.S. Application Data

(60) Provisional application No. 61/368,477, filed on Jul. 28, 2010.

(51) Int. Cl.
*G05B 19/42* (2006.01)
*G05B 19/042* (2006.01)
(Continued)

(52) U.S. Cl.
CPC ........ *G05B 19/042* (2013.01); *C07C 29/1518* (2013.01); *G05B 19/0426* (2013.01);
(Continued)

(58) Field of Classification Search
CPC ...... G06Q 10/087; G06Q 10/08; G06Q 10/06; G06Q 30/06; G06Q 20/203
(Continued)

(56) References Cited

U.S. PATENT DOCUMENTS

| | | | |
|---|---|---|---|
| 5,195,392 A | 3/1993 | Moore et al. | 73/866.5 |
| 5,309,351 A | 5/1994 | McCain et al. | 364/132 |

(Continued)

FOREIGN PATENT DOCUMENTS

| | | |
|---|---|---|
| CN | 101763576 | 6/2010 |
| DE | 10245176 | 4/2004 |

(Continued)

OTHER PUBLICATIONS

Bowe, Michael Joseph. Web-based technologies for command and control. Royal Military College of Canada (Canada), ProQuest Dissertations Publishing, 2002.*

(Continued)

*Primary Examiner* — Fawaad Haider
(74) *Attorney, Agent, or Firm* — Christopher R. Christenson; Kelly, Holt & Christenson PLLC

(57) ABSTRACT

An intrinsically-safe handheld field maintenance tool is provided. The tool includes a process communication module configured to communicate with a field device in accordance with a process industry communication protocol. A controller is coupled to the process communication module and is configured to provide at least one function related to maintenance of the field device. Program instructions embodied on a computer readable medium coupled to the controller, the program instructions causing the controller, when executed by the controller, to provide operator rounds functionality, CMMS/EAM functionality and/or ERP functionality.

5 Claims, 8 Drawing Sheets

(51) Int. Cl.
*G06Q 20/20* (2012.01)
*G06Q 40/04* (2012.01)
*C07C 29/151* (2006.01)
*G06Q 10/06* (2012.01)
*G06Q 30/06* (2012.01)

(52) U.S. Cl.
CPC ..... *G06Q 10/06315* (2013.01); *G06Q 20/204* (2013.01); *G06Q 30/0601* (2013.01); *G06Q 40/04* (2013.01); *G05B 2219/23018* (2013.01); *G05B 2219/23054* (2013.01); *G05B 2219/23126* (2013.01); *G05B 2219/23163* (2013.01); *G05B 2219/23406* (2013.01); *G05B 2219/23445* (2013.01); *G05B 2219/23446* (2013.01); *G05B 2219/24001* (2013.01); *G05B 2219/24056* (2013.01); *G05B 2219/25062* (2013.01); *G05B 2219/25428* (2013.01); *G05B 2219/31121* (2013.01); *G05B 2219/31197* (2013.01); *G05B 2219/31475* (2013.01); *G05B 2219/32007* (2013.01); *G05B 2219/32144* (2013.01); *G05B 2219/32226* (2013.01); *G05B 2219/33331* (2013.01); *G05B 2219/35422* (2013.01); *G05B 2219/35429* (2013.01); *G05B 2219/36122* (2013.01); *G05B 2219/36128* (2013.01); *Y02P 90/14* (2015.11)

(58) Field of Classification Search
USPC .......................................................... 705/28
See application file for complete search history.

(56) References Cited

U.S. PATENT DOCUMENTS

| | | | |
|---|---|---|---|
| 5,442,632 A | 8/1995 | Crowder et al. | 371/20.1 |
| 5,903,455 A | 5/1999 | Sharpe, Jr. et al. | 364/188 |
| 6,033,226 A | 3/2000 | Bullen | 434/219 |
| 6,211,649 B1 | 4/2001 | Matsuda | 320/115 |
| 6,236,223 B1 | 5/2001 | Brady et al. | 324/750.3 |
| 6,377,859 B1 | 4/2002 | Brown et al. | 700/79 |
| 6,594,621 B1 | 7/2003 | Meeker | |
| 6,629,059 B2 | 9/2003 | Borgeson et al. | 702/183 |
| 6,633,782 B1 | 10/2003 | Schleiss et al. | 700/26 |
| 6,725,182 B2 | 4/2004 | Pagnano et al. | 702/188 |
| 6,971,063 B1 | 11/2005 | Rappaport et al. | 715/733 |
| 7,013,184 B2 | 3/2006 | Romagnoli et al. | 700/17 |
| 7,117,122 B2 | 10/2006 | Zielinski et al. | 702/183 |
| 7,120,391 B2 | 10/2006 | Stengele et al. | 455/41.3 |
| 7,188,200 B2 | 3/2007 | Griech | 710/110 |
| 7,337,369 B2 | 2/2008 | Barthel et al. | 714/43 |
| 7,400,255 B2 | 7/2008 | Horch | 340/572.7 |
| 7,421,531 B2 | 9/2008 | Rotvold et al. | 710/315 |
| 7,454,252 B2 | 11/2008 | El-Sayed | 700/21 |
| 7,505,819 B2 | 3/2009 | El-Sayed | 700/21 |
| 7,506,812 B2 | 3/2009 | von Mueller et al. | 235/449 |
| 7,675,406 B2 | 3/2010 | Baier et al. | 340/506 |
| 7,733,833 B2 | 6/2010 | Kalika et al. | 370/338 |
| 7,797,061 B2 | 9/2010 | El-Sayed | 700/21 |
| 8,000,815 B2 | 8/2011 | John et al. | 700/18 |
| 8,036,007 B2 | 10/2011 | Woehrle | 363/65 |
| 8,059,101 B2 | 11/2011 | Westerman et al. | 345/173 |
| 8,060,862 B2 | 11/2011 | Eldridge et al. | 717/121 |
| 8,060,872 B2 | 11/2011 | Da Silva Neto | 717/177 |
| 8,074,172 B2 | 12/2011 | Kocienda et al. | 715/263 |
| 8,126,145 B1 | 2/2012 | Tewari et al. | 380/255 |
| 8,150,462 B2 | 3/2012 | Guenter et al. | 455/557 |
| 8,180,948 B2 | 5/2012 | Kreider et al. | 710/313 |
| 8,224,256 B2 | 7/2012 | Citrano, III et al. | 455/67.11 |
| 8,374,094 B2 | 2/2013 | Law et al. | |
| 2001/0047504 A1 | 11/2001 | Aoyama | 714/799 |
| 2002/0004370 A1 | 1/2002 | Stengele et al. | 455/39 |
| 2002/0007237 A1 | 1/2002 | Phung et al. | 701/33 |
| 2002/0027504 A1 | 3/2002 | Davis et al. | 340/540 |
| 2002/0035495 A1* | 3/2002 | Spira | G06Q 10/04 705/7.36 |
| 2002/0077711 A1* | 6/2002 | Nixon | C10G 11/187 700/51 |
| 2002/0086642 A1 | 7/2002 | Ou et al. | 455/69 |
| 2002/0171558 A1 | 11/2002 | Bartelheim et al. | 340/825.49 |
| 2003/0050737 A1 | 3/2003 | Osann, Jr. | 700/276 |
| 2003/0109937 A1 | 6/2003 | Zielinski et al. | 700/1 |
| 2003/0204373 A1 | 10/2003 | Zielinski et al. | 702/184 |
| 2003/0229472 A1 | 12/2003 | Kantzes et al. | 702/183 |
| 2004/0039458 A1 | 2/2004 | Mathiowetz et al. | 700/17 |
| 2004/0111238 A1 | 6/2004 | Kantzes et al. | 702/183 |
| 2004/0193287 A1 | 9/2004 | Lefebvre et al. | 700/1 |
| 2004/0204193 A1 | 10/2004 | Li et al. | 455/575.1 |
| 2004/0228184 A1 | 11/2004 | Mathiowetz | 365/202 |
| 2004/0230327 A1 | 11/2004 | Opheim et al. | 700/83 |
| 2005/0164684 A1 | 7/2005 | Chen et al. | 455/414.1 |
| 2005/0222698 A1 | 10/2005 | Eryurek et al. | 700/90 |
| 2005/0223120 A1 | 10/2005 | Scharold et al. | 710/1 |
| 2006/0014533 A1 | 1/2006 | Warren | 455/423 |
| 2006/0087402 A1 | 4/2006 | Manning et al. | 340/3.1 |
| 2006/0161393 A1* | 7/2006 | Zielinski | G05B 19/4183 702/184 |
| 2006/0206277 A1 | 9/2006 | Horch | 702/82 |
| 2006/0290496 A1 | 12/2006 | Peeters | 340/572.1 |
| 2006/0291438 A1 | 12/2006 | Karschnia et al. | 370/338 |
| 2007/0161352 A1 | 7/2007 | Dobrowski et al. | 455/69 |
| 2007/0161371 A1 | 7/2007 | Dobrowski et al. | 455/423 |
| 2007/0179645 A1 | 8/2007 | Nixon et al. | 700/83 |
| 2007/0208279 A1 | 9/2007 | Panella et al. | 600/595 |
| 2008/0114911 A1 | 5/2008 | Schumacher | 710/72 |
| 2008/0177969 A1* | 7/2008 | Miriyala et al. | 711/170 |
| 2008/0234837 A1 | 9/2008 | Samudrala et al. | 700/19 |
| 2008/0268784 A1 | 10/2008 | Kantzes et al. | 455/66.1 |
| 2008/0313559 A1* | 12/2008 | Kulus et al. | 715/771 |
| 2009/0030950 A1* | 1/2009 | Maneval | H04L 67/025 |
| 2009/0065578 A1 | 3/2009 | Peterson et al. | 235/382 |
| 2009/0094466 A1 | 4/2009 | Matthew et al. | 713/300 |
| 2009/0125713 A1 | 5/2009 | Karschnia et al. | 713/153 |
| 2009/0171483 A1 | 7/2009 | Scheuermann | 700/83 |
| 2009/0177970 A1 | 7/2009 | Jahl et al. | 715/735 |
| 2009/0271726 A1 | 10/2009 | Gavimath et al. | 715/771 |
| 2009/0284390 A1 | 11/2009 | Lahner et al. | 340/825.49 |
| 2009/0296601 A1 | 12/2009 | Citrano et al. | 370/254 |
| 2009/0326852 A1 | 12/2009 | Vetter et al. | 702/108 |
| 2010/0100766 A1 | 4/2010 | Bengtsson et al. | 714/23 |
| 2010/0114347 A1 | 5/2010 | Dheenathayalan et al. | 700/97 |
| 2010/0114549 A1 | 5/2010 | Kolavi | 703/13 |
| 2010/0145476 A1 | 6/2010 | Junk et al. | 700/7 |
| 2010/0220630 A1 | 9/2010 | Kalika et al. | 370/254 |
| 2010/0290084 A1 | 11/2010 | Russell, III et al. | 358/1.15 |
| 2010/0290351 A1 | 11/2010 | Toepke et al. | 370/250 |
| 2010/0290359 A1 | 11/2010 | Dewey et al. | 370/252 |
| 2010/0293363 A1 | 11/2010 | Meyer et al. | 713/1 |
| 2011/0117529 A1 | 5/2011 | Barash et al. | 434/265 |
| 2011/0238188 A1 | 9/2011 | Washiro | 700/19 |
| 2012/0038458 A1 | 2/2012 | Toepke et al. | 340/6.1 |
| 2012/0038548 A1 | 2/2012 | Toepke et al. | 345/156 |
| 2012/0038760 A1 | 2/2012 | Kantzes et al. | 348/61 |
| 2012/0040316 A1 | 2/2012 | Mathiowetz et al. | 434/219 |
| 2012/0040698 A1 | 2/2012 | Ferguson et al. | 455/457 |
| 2012/0041744 A1 | 2/2012 | Kantzes et al. | 703/13 |

FOREIGN PATENT DOCUMENTS

| | | |
|---|---|---|
| DE | 102007035158 | 1/2009 |
| DE | 102008029406 | 12/2009 |
| DE | 102009028195 | 2/2011 |
| EP | 1515208 | 3/2005 |
| EP | 1916582 | 4/2008 |
| EP | 2026256 | 2/2009 |
| EP | 2071427 | 6/2009 |
| EP | 2077473 | 7/2009 |
| EP | 2148259 | 1/2010 |
| EP | 2204705 | 7/2010 |
| GB | 2382418 | 5/2003 |
| GB | 2 394 124 | 4/2004 |
| JP | 9051583 | 2/1997 |
| JP | H1048099 | 2/1998 |

(56) References Cited

FOREIGN PATENT DOCUMENTS

| | | |
|---|---|---|
| JP | 2001337004 | 7/2001 |
| JP | 2007-91381 | 4/2007 |
| JP | 2008165193 | 7/2008 |
| JP | 2010140484 | 6/2010 |
| KR | 20060078883 | 7/2006 |
| WO | WO 01/35190 | 5/2001 |
| WO | WO 02/086662 | 10/2002 |
| WO | WO 2006/016845 | 2/2006 |
| WO | WO 2008/042074 | 4/2008 |
| WO | WO 2008/077358 | 7/2008 |
| WO | WO 2008/096216 | 8/2008 |
| WO | WO 2008/127632 | 10/2008 |
| WO | WO 2009/003146 | 12/2008 |
| WO | WO 2009/003148 | 12/2008 |
| WO | WO2009/024483 | 2/2009 |
| WO | WO2009026032 | 2/2009 |
| WO | WO 2009/074544 | 6/2009 |

OTHER PUBLICATIONS

First Office Action from counterpart Chinese patent application No. 201180001613,1, dated Feb. 28, 2014. 18 pages.
First Office Action from counterpart Japanese application No. 2013-521965, dated Feb. 4, 2014. 7 pages.
1420 Wireless Gateway. Reference Manual 00809-0100-4420, Rev BA. Aug. 2007. Emerson Process Management.
Invitation to pay additional fees from the related International patent application No. PCT/US2011/045679 dated Aug. 6, 2012.
Invitation to pay additional fees from the related International patent application No. PCT/US2011/045664 dated Aug. 9, 2012.
Invitation to pay additional fees from the related International patent application No. PCT/US2011/045676 dated Jul. 30, 2012.
Lee S W et al: "Honam Petrochemical Corporation Uses Simulator for Ethylene Plant Operator Training", Processing of the Industrial Computing Conference. Houston, Oct. 18-23, 1992. pp. 219-222.
Kurrle H-P et al.: "Trainingssimulator Zur Ausbildung Von Chemikanten und Anlagenfahrern. Otraining Simulator for the Training of Process Workers (Chemikanten) and Operators", Automatisierungstechnische Praxis—ATP, Oldenbourg Indusrieverlag, Munchen, DE, vol. 36, No. 7, Jul. 1, 1994. Abstract, Section 2.
Invitation to pay additional fees from the related International patent application No. PCT/US2011/045665 dated Aug. 23, 2012.
Bushman J B: "Ally: An Operator's Associate for Cooperative Supervisory Control Systems", IEEE Transactions on Systems, Man and Cybernetics, IEEE Inc. New York, US, vol. 23, No. 1, Jan. 1, 1993, pp. 111-128.
First Communication for the related European patent application No. 107302812 dated Oct. 11, 2012.
International Search Report and Written Opinion from the related International patent application No. PCT/US2011/045664 dated Nov. 6, 2012.
International Search Report and Written Opinion from the related International patent application No. PCT/US2011/045679 dated Nov. 6, 2012.
International Search Report and Written Opinion from the related International patent application No. PCT/US2011/045665 dated Nov. 6, 2012.
First Communication from related European patent application No. 107255432 dated Oct. 11, 2012.
First Communication from related European patent application No. 107302796 dated Oct. 19, 2012.
Office Action from related Russian application No. 2011151063 dated Nov. 12, 2012.
First Office Action from related Japanese application No. 2015511048, dated Jan. 29, 2013.
Invitation to Pay Additional Fees for international patent application No. PCT/US2010/034889 dated Sep. 15, 2010.
ABB Limited: "Wireless Instrumentation Jargon Buster". Information bulletin instrumentation ABB No. IB/INST-018, Mar. 3, 2009,
XP002596601. Retrieved from the Internet: URL:http://www05.abb.com/global/scot/scot203.nsf/veritydisplay/be00ec76f07e978c125756e003157b9/$File/IB_INST_018_1.pdf.
Notification of Transmittal of the International Search Report and the Written Opinion from the International Application No. PCT/US2010/021764.
David Gustafsson: "WirelessHART—Implementation and Evaluation on Wireless Sensors". Masters's Degree Project, KTH University, Electrical Engineering, Apr. 1, 2009, pp. 1-39, XP002596602, Stockholm, Sweden. Retrieved from the Internet: URL:http://www.ee.kth.se/php/modules/publications/reports/2009/XR-EE-RT%202009:003.pdf.
Notification of Transmittal of the International Search Report and the Written Opinion for the International application No. PCT/US2010/034848 dated Aug. 26, 2010.
Possio Bluetooth to WLANn Gateway PX20: Full Product Description retrieved from http://www.blueunplugged.com/p.aspx?p=105816.
1420 Wireless Gateway: Product Data Sheet 00813-0100-4420, Rev BA Mar. 2008. Emerson Process Management.
Smart Wireless Gateway (WiretessHART™). Quick Installation Guide 00825-0200-4420, Rev BA. Aug. 2009. Emerson Process Management.
Rosemount 3051S Wireless Series Scalable Pressure, Flow, and Level Solutions. Reference Manual 00809-0100-4802, rev BA. Aug. 2007. Emerson Process Management.
EPO Communication pursuant to Rules 161(1) and 162 EPC for European patent application No. 10701430.0 dated Aug. 30, 2011.
Invitation to Pay Additional Fees for international patent application No. PCT/US2010/034949 dated Sep. 17, 2010.
Technical Data Sheet: VIATOR® USB HART® Interface (Model 010031). MACTek Measurement and Control Technologies.
VIATOR® Bluetooth® Wireless Technology Interface for use with HART field devices. MACTek Measurement and Control Technologies retrieved from www.mactekcorp.com/product5.htm.
Product Data Sheet: VIATOR RS232. MACTek Measurement and Control Technologies retrieved from www.mactekcorp.com/product1.htm.
Notification of Transmittal of the International Search Report and the Written Opinion from the International Application No. PCT/US2010/034889.
Notification of Transmittal of the International Search Report and the Written Opinion from the International Application No. PCT/US2010/034949.
EPO Communication from related European application No. 10730279.6 dated Jan. 13, 2012.
EPO Communication from related European application No. 10730281.2 dated Jan. 13, 2012.
EPO Communication from related European application No. 10725543.2 dated Jan. 12, 2012.
Rosemount 3051SMV Quick Installation Guide 00825-0100-4803 Rev BA. Apr. 2011.
Invitation to Pay Additional Fees from the International Application No. PCT/US2011/045673 dated Jan. 16, 2012.
Notification of Transmittal of the International Search Report and the Written Opinion from the International Application No. PCT/US2011/045680 dated Jul. 6, 2012.
Notification of Transmittal of the International Search Report and the Written Opinion from the International Application No. PCT/US2011/045681 dated Jan. 5, 2012.
475 Field Communicator. User's Guide XP007919976. Aug. 2009. www.fieldcommunicator.com by Emerson Process Management.
First Office Action from Canadian Application No. 2,806,560 dated Jul. 28, 2014, 4 pages.
Notification on Results of Patentability Check from Russian Patent Application No. 2013108799, dated Jun. 26th, 2014. 11 pages with English Translation.
Decision of Rejection from Japanese Patent Application No. 2013-521965 dated Nov. 25, 2014, 6 pages.
Second Office Action from Counterpart Chinese Patent Application No. 201180001613.1, dated Dec. 8, 2014 with English Translation, 8 pages.

(56) References Cited

OTHER PUBLICATIONS

The Third Office Action for Chinese Patent Application No. 20 80001613.1 dated Jun. 2, 2015. 7 pages.
Fourth Office Action for Chinese Patent Application No. 201180001613.1 dated Jan. 20, 2016, 7 pages.
Office Action for Canadian Counterpart Application No. 2,806,560 dated Oct. 5, 2015, 6 pages.
Office Action for Canadian Patent Application No. 2,806,560 dated Jun. 10, 2016, 5 pages.
EPO Communication pursuant to Article 94(3) EPC for European Patent Application No. 11739255.5 dated Jun. 30, 2017, 9 pages.
Notification of Reasons for Rejection for Japanese Patent Application No. 2013-521965 dated Sep. 15, 2015, 5 pages with English Translation.

* cited by examiner

HANDHELD FIELD MAINTENANCE TOOL WITH INTEGRATION TO EXTERNAL SOFTWARE APPLICATION

CROSS-REFERENCE TO RELATED APPLICATION

The present application is based on and claims the benefit of U.S. provisional patent application Ser. No. 61/368,477, filed Jul. 28, 2010, the content of which is hereby incorporated by reference in its entirety.

BACKGROUND

Handheld field maintenance tools are known. Such tools are highly useful in the process control and measurement industry to allow operators to conveniently communicate with and/or interrogate field devices in a given process installation. Examples of such process installations include petroleum, pharmaceutical, chemical, pulp, and other fluid processing installations. In such installations, the process control and measurement network may include tens or even hundreds of various field devices which periodically require maintenance to ensure that such devices are functioning properly and/or calibrated. Moreover, when one or more errors in the process control and measurement installation are detected, the use of a handheld field maintenance tool allows a technician to quickly diagnose such errors in the field. Handheld field maintenance tools are generally used to configure, calibrate, and diagnose problems relative to intelligent field devices using digital process communication protocols.

Since at least some process installations may involve highly volatile, or even explosive, environments, it is often beneficial, or even required, for field devices and the handheld field maintenance tools used with such field devices to comply with intrinsic safety requirements. These requirements help ensure that compliant electrical devices will not generate a source of ignition even under fault conditions. One example of Intrinsic Safety requirements is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998. An example of a handheld field maintenance tool that complies with intrinsic safety requirements includes that sold under trade designation Model 475 Field Communicator, available from Emerson Process Management of Austin, Tex.

SUMMARY

An intrinsically-safe handheld field maintenance tool is provided. The tool includes a process communication module configured to communicate with a field device in accordance with a process industry communication protocol. A controller is coupled to the process communication module and is configured to provide at least one function related to maintenance of the field device. Program instructions embodied on a computer readable medium coupled to the controller, the program instructions causing the controller, when executed by the controller, to provide operator rounds functionality, CMMS/EAM functionality and/or ERP functionality.

DETAILED DESCRIPTION

Figure 1A:
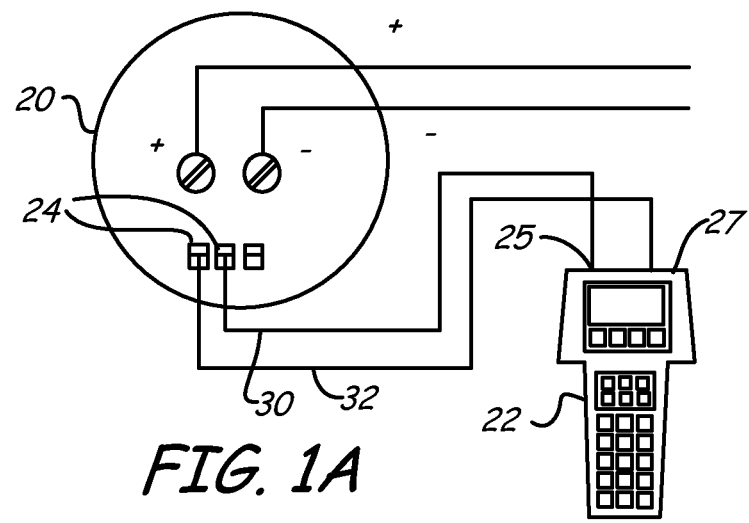
FIGS. 1A and 1B are diagrammatic views of a handheld field maintenance tool with which embodiments of the invention are particularly useful.
Figure 1B:
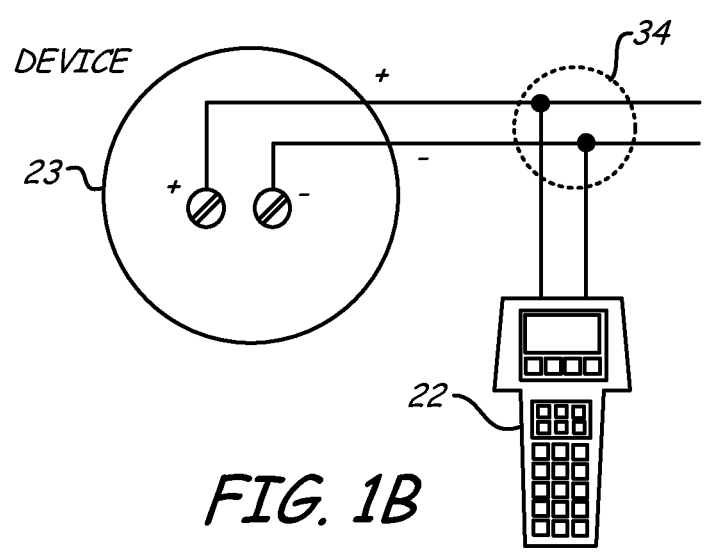

FIGS. 1A and 1B are diagrammatic views of a handheld field maintenance tool 22 coupled to field devices 20, 23. As shown in FIG. 1A, handheld field maintenance tool 22 includes a pair of terminals 25, 27 that couple to test leads 30, 32, respectively, which are then coupled to terminals 24 of field device 20. Terminals 24 may be dedicated terminals to allow such a handheld field maintenance tool to couple to device 20 and interact with device 20. The utilization of terminals 25, 27 to couple to field device illustrates an example of a wired connection between handheld field maintenance tool 22 and field device 20.

FIG. 1B shows an alternate arrangement where handheld field maintenance tool 22 couples directly to the process control loop 34 to which field device 23 is coupled. In either case, the wired connection between the handheld field maintenance tool and the field device allows the handheld field maintenance tool to interact with the desired field device 20, 23.

Figure 2:
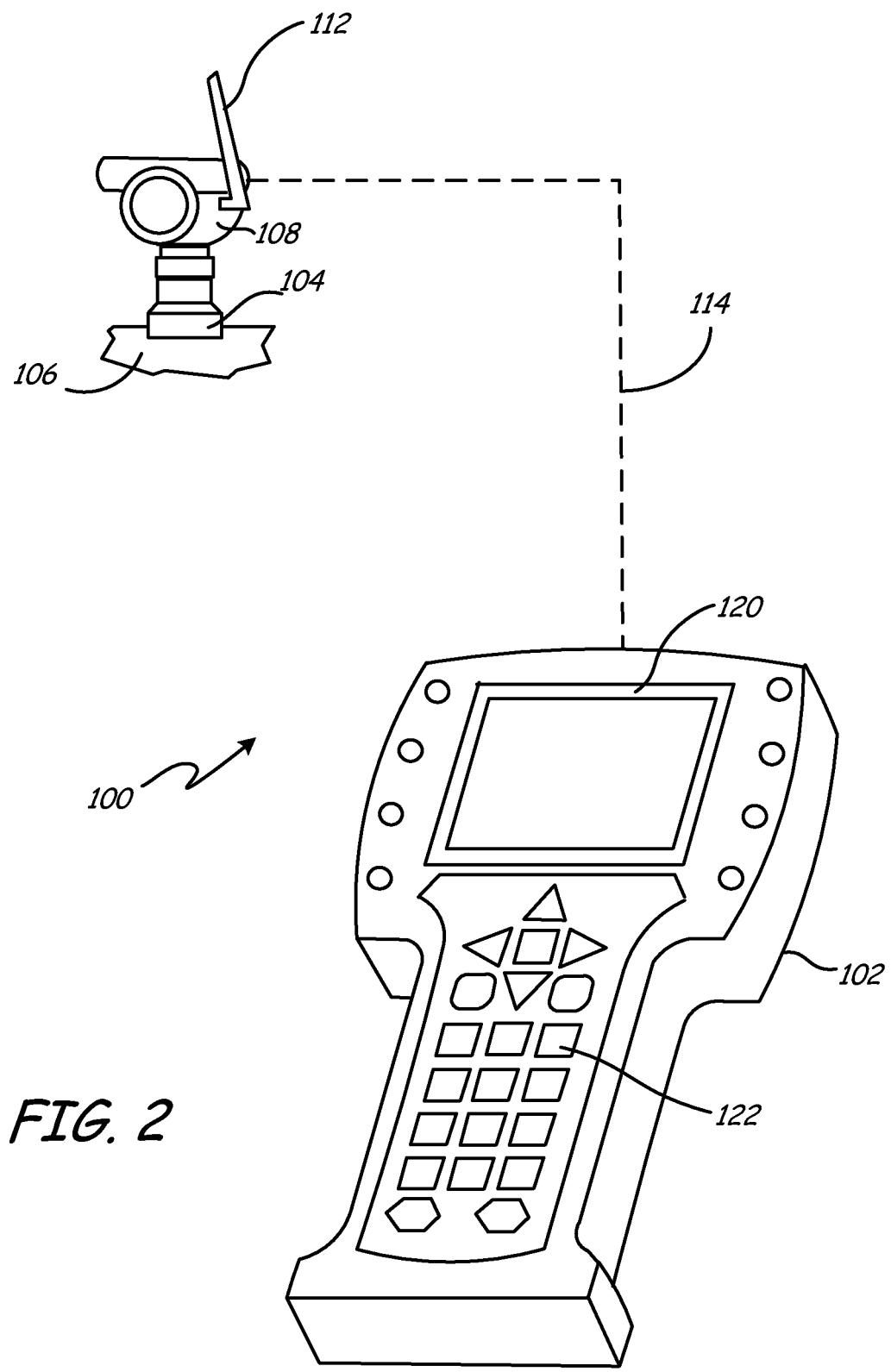
FIG. 2 is a diagrammatic view of a handheld field maintenance tool with which embodiments of the present invention are particularly useful.

FIG. 2 is a diagrammatic view of handheld field maintenance tool 102 interacting with wireless field device 104. System 100 includes handheld field maintenance tool 102 communicating with field device 104. Handheld field maintenance tool 102 is communicatively coupled to field device 104 via communication link 114. Communication link 114 can take any suitable form including wired connections as shown in FIGS. 1A and 1B, as well as wireless communication techniques that are currently being used or being developed. Handheld field maintenance tool 102 allows a technician to interact with field device 104 to configure, calibrate, and/or diagnose problems with respect to field device 104 using a digital process communication protocol such as FOUNDATION™ Fieldbus and/or the HART® protocol. Handheld field maintenance tools, such as tool 102 can be used to save configuration data from field devices, such as field device 104.

Field device 104 may be any device that senses a variable in the process and transmits information related to the variable over a process communication loop; such as a pressure or temperature. Field device 104 may also be a device that receives information from a process communication loop and sets a physical parameter, such as a valve closure, based on the information. Field device 104 is depicted as an industrial process fluid pressure transmitter having a pressure manifold 106 coupled thereto, and an electronics enclosure 108. Field device 104 is provided for illustrative purposes only. In reality, field device 104 may be any industrial device, such as a process fluid temperature transmitter, process fluid level transmitter, process fluid flow transmitter, valve controller, or any other device that is useful in the measurement and/or control of industrial processes.

Handheld field maintenance tool 102 generally includes a user interface that comprises a display 120 as well as a number of user input buttons 122. Display 120 may be any suitable display such as an active-matrix liquid crystal display, or any other suitable display that is able to provide useful information. Buttons 122 may comprise any suitable arrangement of buttons relative to any number of functions to which the handheld field maintenance tool may be directed. Buttons 122 may comprise a numeric keypad, an alphanumeric keypad, any suitable number of custom functions and/or navigation buttons, or any combination thereof.

Figure 3:
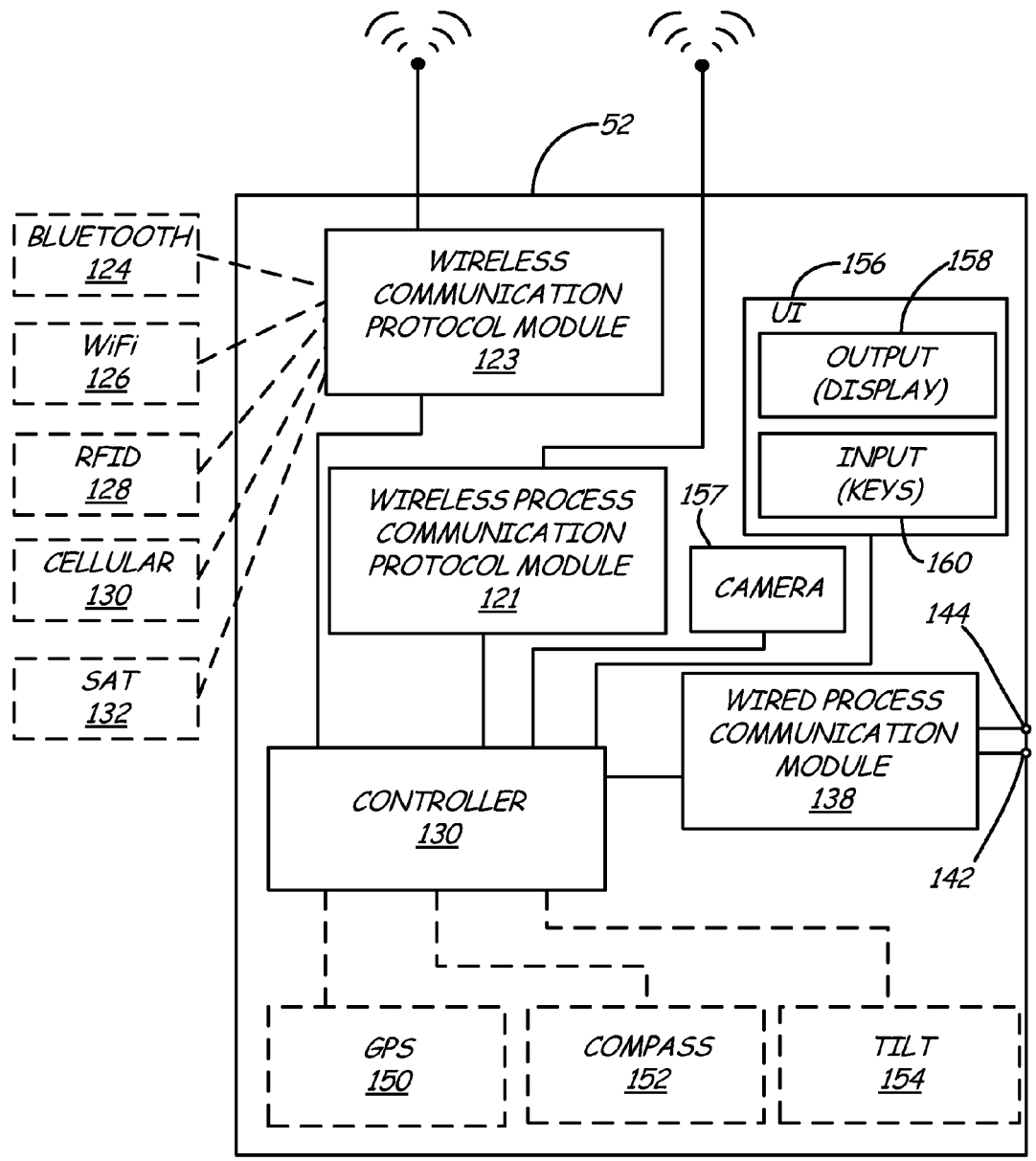
FIG. 3 is a block diagram of a handheld field maintenance tool in accordance with an embodiment of the present invention.

FIG. 3 is a diagrammatic system block diagram of a handheld field maintenance tool in accordance with the embodiment of the present invention. It is preferred that tool 52 comply with at least one intrinsic safety specification, such as that listed above, in order to help ensure safety in potentially explosive environments. Handheld field maintenance tool 52 includes at least one wireless process communication module 121. Suitable examples for wireless process communication module 121 include a module that generates and/or receives proper signals in accordance with a known wireless communication protocol, such as the known WirelessHART protocol (IEC 62591). Another wireless process communication protocol is set forth in ISA100.11a. While FIG. 3 shows a single wireless process communication module 121, it is expressly contemplated that any suitable number of wireless process communication modules can be used to communicate in accordance with various wireless process communication protocols now in existence or later developed.

Handheld field maintenance tool 52 also includes at least one secondary wireless communication protocol module 123. Wireless communication protocol module 123 can communicate in accordance with one or more of the options shown in phantom in FIG. 3. Specifically, wireless communication protocol module 123 may communicate in accordance with a Bluetooth specification 124 (such as Bluetooth Specification 2.1 rated at Power Class 2; a Wi-Fi specification 126 (such as IEEE 802.11.a/b/g/n); a known RFID specification 128; cellular communication techniques 130 (such as GSM/CDMA); and/or satellite communication 132. These communication techniques and methodologies allow handheld field maintenance tool 52 to communicate directly with a wireless gateway or other suitable device either via direct wireless communication, or using the Internet. While one wireless communication protocol module 123 is shown in FIG. 3, any suitable number may be used. Each of the wireless process communication protocol module 121 and wireless communication protocol module 123 is coupled to controller 130 which is also coupled to the wired process communication module 138. Controller 130 is preferably a microprocessor that executes a sequence of instructions stored therein, or in memory coupled to controller 130, to perform handheld field maintenance tasks. Wired process communication module 138 allows handheld field maintenance tool 52 to be physically coupled via a wired connection at terminals 142, 144 to a field device. Examples of suitable wired process communication include the Highway Addressable Remote Transducer (HART®) protocol, the FOUNDATION™ Fieldbus protocol, Profibus and others.

Handheld field maintenance tool 52 includes a user interface module 156 for generating a user interface using display 120 and keys 122. Module 156 can include suitable display driver circuitry 158 and/or memory to interact with display 120. Module 156 also includes input circuitry 160 which is configured to interact with buttons 122 to receive user input. Additionally, in embodiments where display 120 includes a touchscreen, module 160 can include circuitry to generate user input data to controller 130 based upon a user's touch and/or gestures received by the touchscreen.

Handheld field maintenance tool 52 can include a number of additional items that facilitate additional functionality. Specifically, tool 52 can include a position detection module, such as GPS module 150. GPS module 150 can be configured to additionally use the Wide Area Augmentation System (WAAS) for improved accuracy and/or can be configured to operate using differential GPS techniques as appropriate. Module 150 is coupled to controller 130 to provide controller 130 with an indication of the geographic position of tool 52. While position detection module 150 is preferably an internal component of tool 52, it may be external and communicatively coupled thereto using a suitable wireless or wired communication protocol, such as Bluetooth 124, RFID 128, et cetera. Further still, while position detection module 150 is generally described as GPS module 150, other techniques for triangulating the position of the handheld field maintenance tool based upon relative strength of wireless communication with wireless transceivers having known fixed positions can be employed. Examples of such wireless triangulation techniques include triangulation of the position of handheld field maintenance tool 52 based upon communication with three or more fixed-position WiFi communication points, or access points. Further still, as set forth above, embodiments of the present invention may include the ability to employ one or more wireless process communication protocol modules, such as module 121. Such triangulation techniques can also be employed if a suitable number of wireless interactions with fixed-position wireless field devices can be achieved. Finally, while the various methods provided for obtaining the position of handheld field maintenance tool 52 are described above, they can also be used in conjunction with one another to provide additional accuracy and/or redundancy. Additionally, tool 52 also preferably comprises compass module 152 coupled to controller 130 such that tool 52 can indicate the compass direction in which it is pointing. Finally, tool 52 can also include tilt module 154 coupled to controller 130 to provide an indication to controller 130 relative to an angle of inclination of tool 52 relative to gravity. However, additional axes of sensing are also contemplated.

The positional location module 150, compass module 152 and tilt module 154 are particularly useful where a handheld field maintenance tool helps a technician or engineer find the physical location of a wireless field device in the field. An oil refinery is often a very large process installation with many field devices positioned at various locations, some of which may not be readily visible Maintenance technicians, engineers, and operations personnel are sometimes required to do periodic, scheduled operator/maintenance rounding, to both verify that devices, equipment, processes, et cetera are functioning correctly, and to look for problems that need to be addressed. Most often, these rounds involve executing manual procedures, taking measurements, observing behavior, and recording results, which are collected and maintained in a historical repository. Current practice in some cases is for these rounding procedures to be documented in paper procedures, and the results to be manually recorded on paper log sheets. In other cases, this information can be stored electronically using an electronic handheld device made for that purpose. Thus, personnel required to travel into the field to interact with field devices, and other equipment, must often carry a handheld field maintenance tool to actually interact with such field devices, and further carry a manual log, or an additional electronic device to record the results and/or interactions with the various field devices. Additionally, some maintenance technicians, engineers, and operations personnel are sometimes required to access enterprise software (ERP) from the field. For such personnel that need to do both interactions with ERP software, and handheld field maintenance, the current practice is to carry a handheld field maintenance tool for online device tasks, and a second handheld electronic device for access to enterprise software. Thus, it is conceivable that a single person venturing into the field would have no less than three distinct electronic devices all purpose-built for specific tasks. Such cargo diminishes the efficiency of the field technician, and also requires the technician to interact with various different disparate devices, thereby increasing the potential for errors.

In accordance with an embodiment of the present invention, an intrinsically-safe handheld field maintenance tool is provided with additional software functionality to provide operator/maintenance rounds functionality, automatic communication with enterprise software (ERP), and automatic communication with a computerized maintenance management system (CMMS) or enterprise asset management system, or both.

Figure 4:
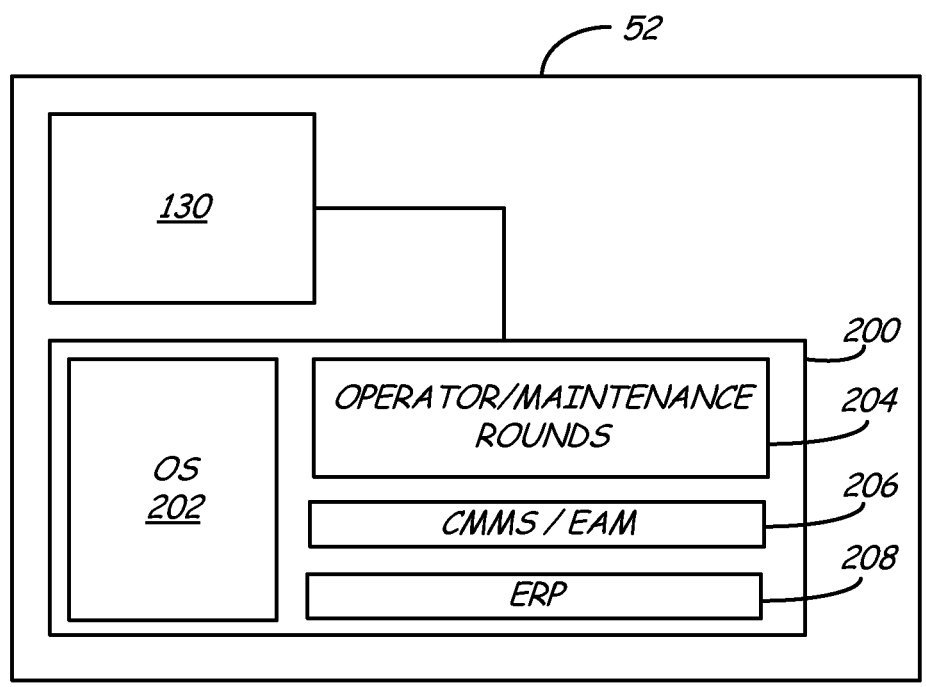
FIG. 4 is a diagrammatic view of handheld field maintenance tool having controller coupled to memory containing program instructions in accordance with an embodiment of the present invention.

FIG. 4 is a diagrammatic view of handheld field maintenance tool 52 having controller 130 coupled to memory 200. Memory 200 preferably includes at least some non-volatile memory, such as flash memory, and at least some volatile memory, such as random access memory. Moreover, while memory 200 is shown separate from controller 130, in at least some embodiments, memory 200 may be a component of controller 130. Memory 200 preferably stores operating system information 202 which includes program instructions which when executed by controller 130 cause controller 130 to provide a software platform upon which various programs can execute and have access to other hardware components, such as GPS module 150, compass module 152, tilt sensor 154, camera 157, user interface 156 as well as any and all communication protocol modules 124, 126, 128, 130, 132. Suitable examples of operating system 202 include Windows CE, available from Microsoft Corporation of Redmond, Wash., the Android operating system, available from Google, Inc., or any other suitable operating system. Memory 200 also preferably includes operator/maintenance rounds application module 204, CMMS/EAM module 206, and ERP module 208. When invoked, or otherwise executed by controller 130, operator/maintenance rounds module 204 causes the handheld field maintenance tool to facilitate operator/maintenance rounds functions of the technician. This integration can be done in varying degrees which progressively may add more value to the end user. In one embodiment, integration simply involves the ability to run operator/maintenance rounds module 204 on handheld field maintenance tool 52. In another embodiment, the integration can include tying together the operator/maintenance rounds procedures that require online measurements, data, et cetera, with the ability to communicate online with the field device to gather such data, thereby consolidating the functionality into a single workflow on the handheld field maintenance tool. This tighter integration could potentially result in a number of end user benefits. For example, the user would not need to carry multiple electronic devices, or paper logs. Further, the tighter integration potentially offers additional time savings as the technician now has two related applications tied together on one consolidated flow. Moreover, data measured, or otherwise received from a field device can be entered directly into the rounds application without requiring the user to actually key the data in. This may substantially reduce technician time as well as reduce the potential for inadvertent data entry errors. Moreover, rounds application module 204 may further communicate with a remote asset management system, or high level information system, to obtain routes, procedures and other data, as well as to save information obtained or stored within rounds application module 204.

Figure 5:
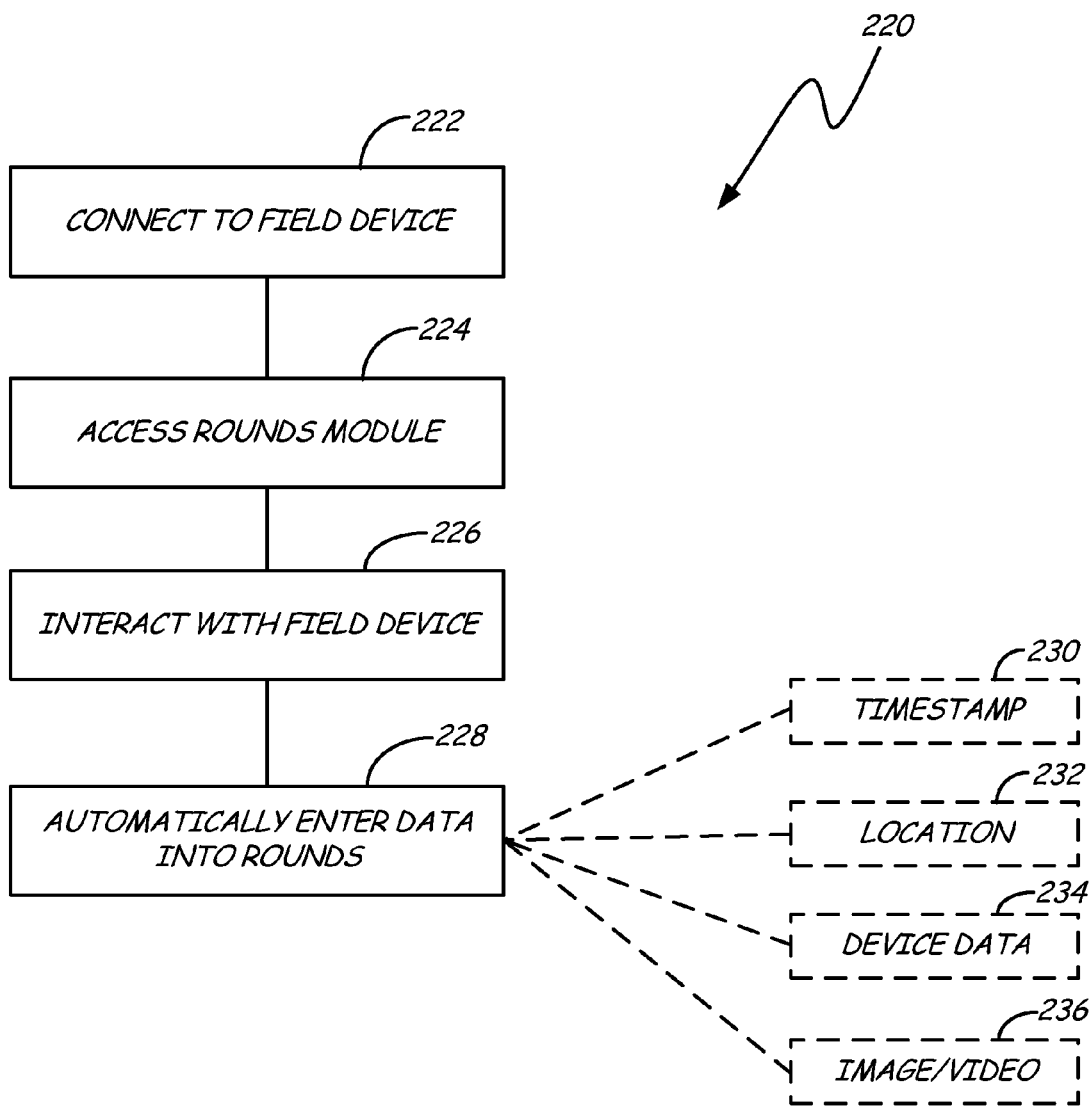
FIG. 5 is a flow diagram of a method of performing field maintenance and automatically entering rounds data in accordance with an embodiment of the present invention.

FIG. 5 is a flow diagram of a method of performing field maintenance and automatically entering rounds data in accordance with an embodiment of the present invention. Method 220 begins at block 222 where a handheld field maintenance device is coupled to a field device. Once such coupling occurs, method 220 continues at block 224 where the handheld field maintenance tool accesses rounds module 204. Such access can include controller 130 invoking application 204, transferring focus to application 204, or simply generating a communication channel to module 204 through operating system 202. Next, at block 226, the handheld field maintenance tool interacts with the field device. Such interaction can include any communication, measurements, or other electronic interactions related to maintenance, troubleshooting, configuration, calibration, installation, et cetera. At block 228, at least some information related to the field device is automatically entered into rounds application 204, as indicated at block 228. Such information can include, for example, time stamp information 230 indicating date and/or time when the handheld field maintenance tool connected to the field device at block 222. Moreover, the data can also include location information 232, which location information can be supplied by GPS module 150. The automatically-entered data can also include any or all electronic data received from and/or sent to the field device by the handheld field maintenance tool, as indicated at block 234. Further still, image/video information acquired by camera 157 of field device 222 can also be entered into rounds application 204, as indicated at block 236. In this manner, rounds application 204 is automatically, at least to some extent, provided with data during the technician's rounds in the field while interacting with various field devices. Preferably, the data acquired by rounds application 204 can be automatically uploaded to a suitable asset management system or higher level information system using wireless communication. Further, the asset management system of higher level information system can be accessed prior to method 220 to actually receive, preferably wirelessly, route information and/or one or more procedures to be performed while the technician is in the field.

Figure 6:
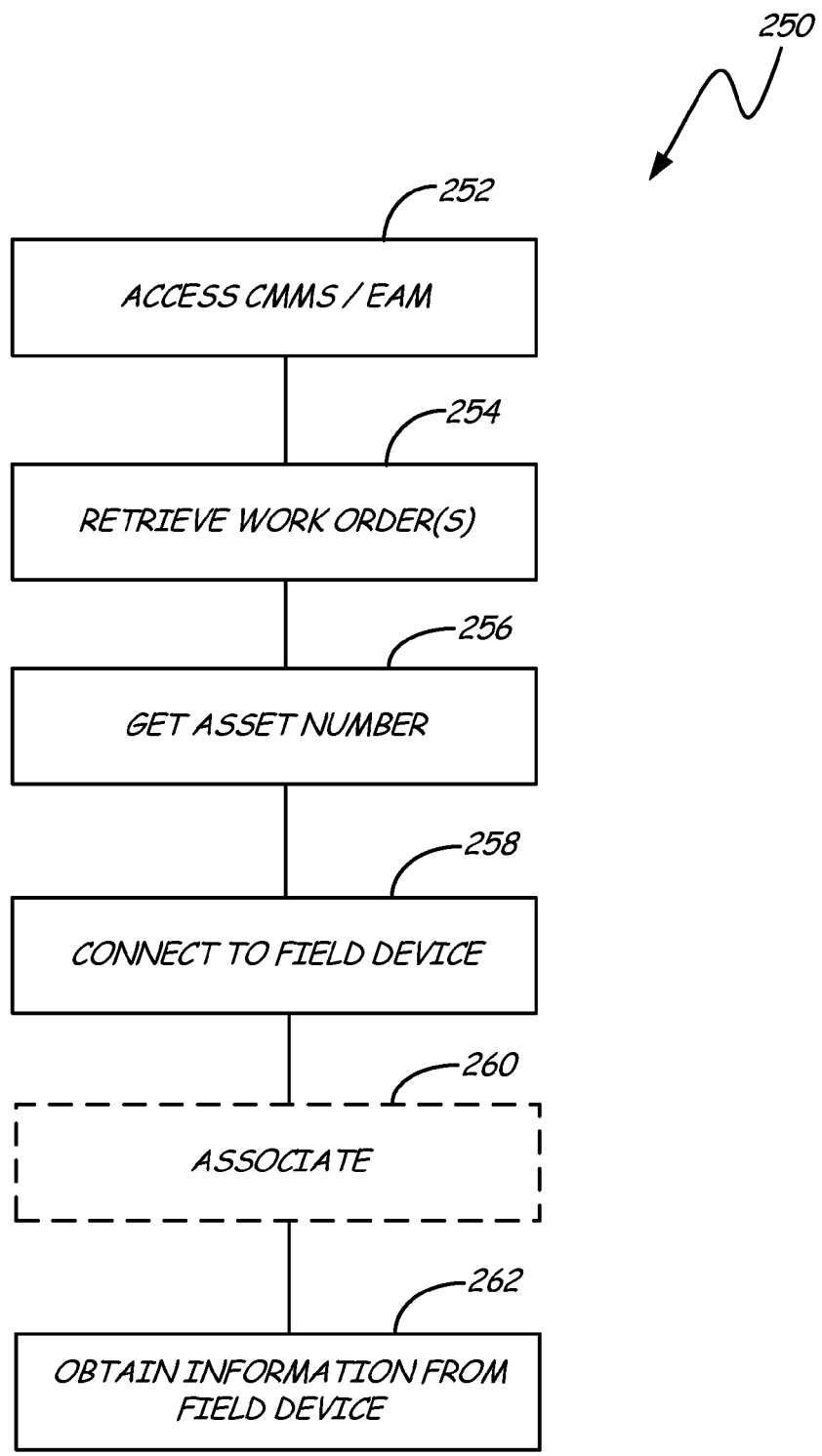
FIG. 6 is a flow diagram of a method of performing field maintenance via remote access to a CMMS/EAM system in accordance with an embodiment of the present invention.

FIG. 6 is a flow diagram of a method of performing field maintenance via remote access to a CMMS/EAM system in accordance with an embodiment of the present invention.

Method 250 begins at block 252 where CMMS/EAM module 206 is executed by controller 130 to provide CMMS/EAM software functions on handheld field maintenance tool 52. Software 206 preferably creates, or otherwise employs, a communication link or channel with a host CMMS/EAM software module operating at a remote location by virtue of a wireless connection, such as WiFi, cellular, satellite, WiMax, or any combination thereof. At block 254, the handheld field maintenance tool retrieves one or more work orders as generated by the CMMS/EAM system. Each work order will include an asset number. The asset number may be related to one or more field devices. Typically, the asset number itself is not associated with a field device's tag or unique ID. In accordance with an embodiment of the present invention, when the technician connects the handheld field maintenance tool 52 to the selected field device, as indicated at block 258, the handheld field maintenance tool 52 preferably associates the unique ID or field device tag with the asset number for which the work order is being executed. Preferably, this association is stored in the handheld field maintenance tool and optionally uploaded from the CMMS/EAM host system, as indicated at block 260. At block 262, handheld field maintenance tool 52 obtains information from the field device in accordance with the specification set forth by the work order. More preferably, information obtained from the field device will preferably be uploaded directly into the CMMS/EAM host software system by virtue of the wireless data connection using wireless communication protocol module 123. After this associating is done, the handheld field maintenance tool will present the technician with the appropriate work order and associated instructions documented in the work order. The technician will performed his or her tasks per the instructions documented in the word order. Those tasks may include executing manual or automated procedures and techniques to perform field device diagnostics, repairs, configuration, calibration, et cetera. Some of those tasks and procedures may involve online activities using the handheld field maintenance tool. In accordance with an embodiment of the present invention, the results of those activities, such as configuration changes, status changes, et cetera would preferably be associated and populated into the work order in the form of notes or results. Upon completion of part or all of the work order, the work order results information, including status, notes, et cetera is preferably uploaded back to the CMMS/EAM system.

Figure 7:
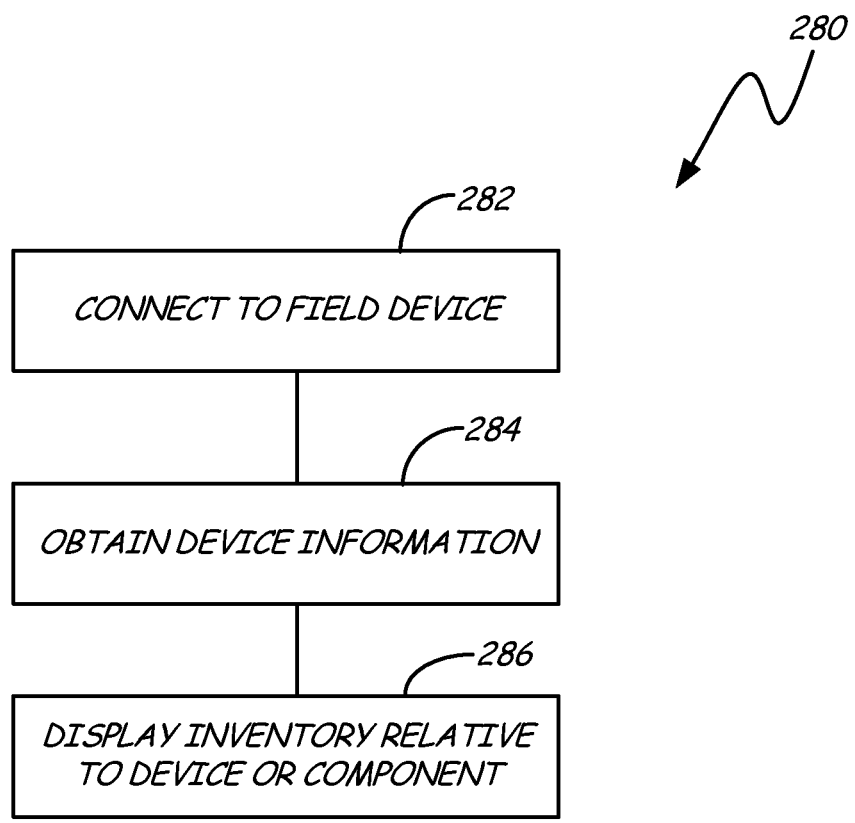
FIG. 7 is a flow diagram of a method of performing field maintenance using communication to an enterprise software (ERP) system in accordance with an embodiment of the present invention.

FIG. 7 is a flow diagram of a method of performing field maintenance using communication to an enterprise software (ERP) system in accordance with an embodiment of the present invention. Method 280 begins at block 282 when a technician couples, or otherwise connects, handheld field maintenance tool 52 to a field device. Next, at block 284, the handheld field maintenance device obtains device information relative to the connected field device. For example, device information can include the tag, or other unique identification of the field device, the manufacturer of the field device, the device type, device revision info, et cetera. Moreover, in embodiments where such information of the field device is embodied within an RFID tag located on, in, or proximate the field device, the RFID information can simply be read by the handheld field maintenance tool using RFID module 128 in the handheld field maintenance tool. In such instances, a direct physical coupling to the field device may not be required. In any event, once handheld field maintenance tool 52 has device information, as indicated at block 284, the device information is used to query, or otherwise access, an enterprise software host located remotely from the field device and the handheld field maintenance tool. Preferably, this communication is performed using wireless communication, such as WiFi, cellular, satellite, WiMax, et cetera. Communication with the ERP host system allows the handheld field maintenance tool 52 to display inventory relative to the field device, and/or components or subsystems thereof, as indicated at block 286. Embodiments of the present invention can also be practiced where a technician simply enters a part number or device number into th handheld field maintenance tool to query inventory. Additionally, it is expressly contemplated that more than one query can be generated. For example, a first query can be submitted to a local inventory control system, while a second query can be submitted to an off-site inventory control system. The local inventory can be queried to determine available quantities of parts or devices, and the locations in the plant of such parts or devices. The remote inventory query can be useful to provide price and availability on purchase parts and devices from external sources or suppliers. Moreover, it is also contemplated that a purchase from such a remote supplier can be facilitated using a handheld field maintenance tool in accordance with embodiments of the present invention. The display of inventory (an entire field device, subsystems, and/or components thereof) can also be supplemented with the number of available units in the inventory, locations within the inventory, and contact information for such devices, subsystems, and/or components.

Figure 8:
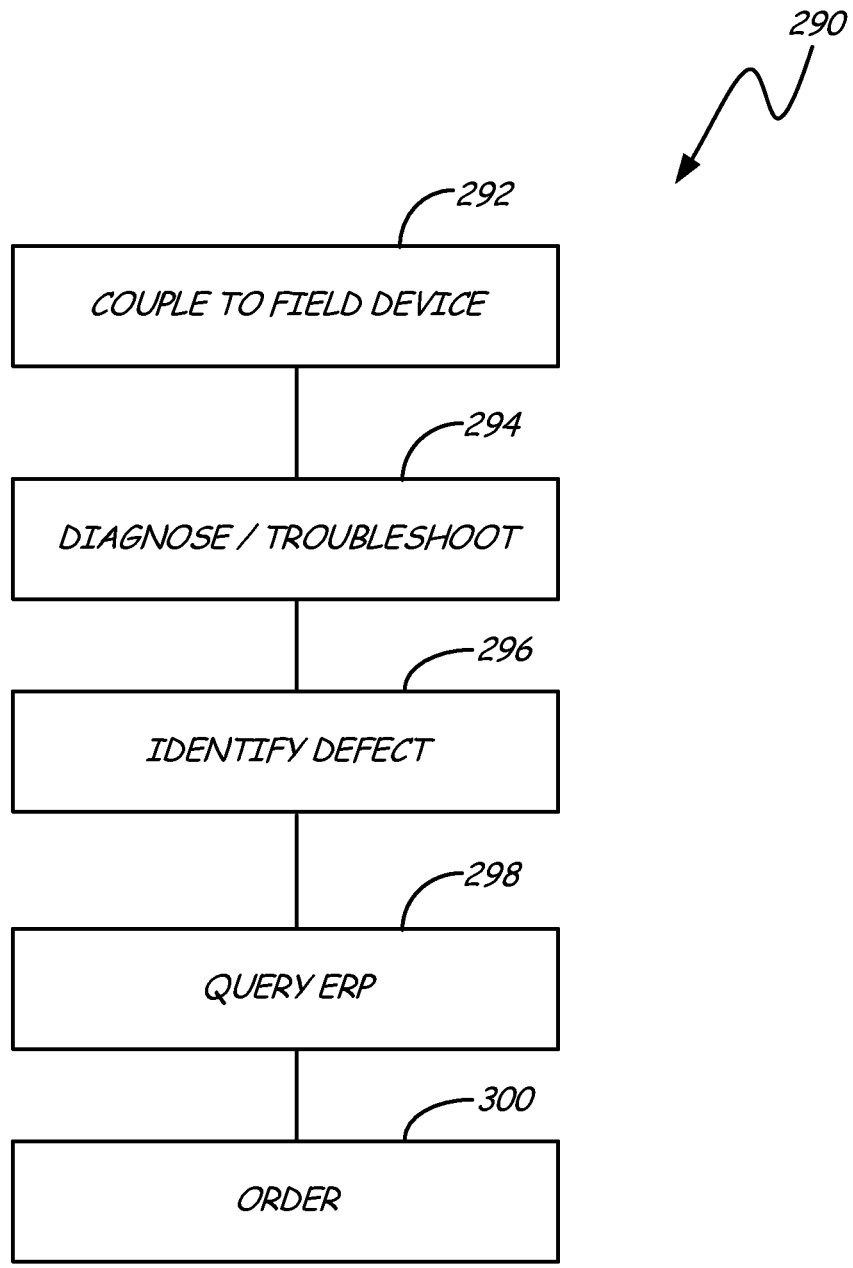
FIG. 8 is a flow diagram of a method of performing field maintenance in conjunction with communicating within ERP system in accordance with an embodiment of the present invention.

FIG. 8 is a flow diagram of a method of performing field maintenance in conjunction with communicating with an ERP system in accordance with an embodiment of the present invention. Method 290 begins at block 292 where a handheld field maintenance device is coupled to a field device. Next, at block 294, the handheld field maintenance tool, technician, and/or both uses the handheld field maintenance tool 52 to diagnose or otherwise troubleshoot a problem relative to the field device. At block 296, a defect is identified that is causing the problem diagnosed in block 294. At block 298, the handheld field maintenance tool 52 queries, by virtue of wireless communication through wireless communication protocol module 123, a remote ERP host system relative to the defective component, subsystem, or device. Through such communication, handheld field maintenance tool 52 receives information from the ERP host system indicating the number of available spare components, subsystems, or devices, locations relative to each such unit, and contact location for such units. Next, at block 300, the technician can automatically order a replacement component, subsystem, or device directly through the remotely-connected ERP host system using handheld field maintenance tool 52. Thus, a technician need not identify a component, lookup the specific part number of the component, and then re-key the part number into an ERP system to order the component. Accordingly, time is saved and opportunities for data errors are reduced.

There are a number of situations where a field maintenance technician may be aided by embodiments of the present invention. For example, the technician may be diagnosing a problem and discover that he or she requires new parts or a new field device. In such instance, the technician can simply order the required parts or device while in the field. Another situation where embodiments of the present invention are particularly useful is where some sort of maintenance activity, such as an outage, is being planned and inventory status and/or availability or components or devices must be determined.

Although the present invention has been described with reference to particular embodiments, workers skilled in the art will recognize that changes may be made in form and detail without departing from the spirit and scope of the invention.

What is claimed is:

1. An intrinsically-safe handheld field maintenance tool comprising:
    a process communication module configured to communicate with a field device in accordance with a process industry communication protocol;
    a controller coupled to the process communication module, the controller being configured to provide at least one maintenance function related to the field device; and
    program instructions embodied on a computer readable medium coupled to the controller, the program instructions causing the controller, when executed, to:
        obtain device information relative to the field device wherein the device information is obtained using near field communication between the intrinsically-safe handheld field maintenance tool and the field device, and wherein the obtained device information provides at least some diagnostic information about the field device, and wherein the maintenance tool identifies a defective component of the field device based on the obtained device information;
        access, using the communication module, an ERP host system located remotely from the field device and the maintenance tool;
        execute a query using a wireless communication with a remote ERP host system, wherein the query is based on the identified defective component of the field device;
        receive a remote inventory parameter relative to the field device, wherein the controller is configured to receive a user input to the intrinsically-safe handheld field maintenance tool and responsively generate an order for a unit stored in inventory, which is displayed on the intrinsically-safe handheld field maintenance tool, and wherein the remote inventory parameter corresponds to the identified defective component of the field device; and
        provide a display of the remote inventory parameter.

2. The intrinsically-safe handheld field maintenance tool of claim 1, wherein the remote inventory parameter includes a number of units available.

3. The intrinsically-safe handheld field maintenance tool of claim 1, wherein the remote inventory parameter includes a location of a unit stored in inventory.

4. The intrinsically-safe handheld field maintenance tool of claim 1, wherein the remote inventory parameter includes contact information relative to a unit stored in inventory.

5. The intrinsically-safe handheld field maintenance tool of claim 1, wherein the device information includes a device tag.

\* \* \* \* \*